(12) United States Patent
Stone et al.

(10) Patent No.: US 6,929,604 B2
(45) Date of Patent: *Aug. 16, 2005

(54) OPTIC FOR INDUSTRIAL ENDOSCOPE/ BORESCOPE WITH NARROW FIELD OF VIEW AND LOW DISTORTION

(75) Inventors: Gary F. Stone, Livermore, CA (US); James E. Trebes, Livermore, CA (US)

(73) Assignee: The Regents of the University of California, Oakland, CA (US)

(*) Notice: Subject to any disclaimer, the term of this patent is extended or adjusted under 35 U.S.C. 154(b) by 149 days.

This patent is subject to a terminal disclaimer.

(21) Appl. No.: 10/236,304

(22) Filed: Sep. 4, 2002

(65) Prior Publication Data

US 2004/0044271 A1 Mar. 4, 2004

(51) Int. Cl.[7] .............................. A61B 1/04; G02B 9/02; G01B 11/30
(52) U.S. Cl. ...................... 600/176; 359/718; 356/600
(58) Field of Search ......................... 359/718, 793–796, 359/362, 435, 646, 717, 434; 356/600, 601, 609, 241.1; 600/176, 182

(56) References Cited

U.S. PATENT DOCUMENTS

| | | | | |
|---|---|---|---|---|
| 3,640,606 A | * | 2/1972 | Conrad | 359/789 |
| 3,868,504 A | * | 2/1975 | Anderson | 250/214 VT |
| 5,210,646 A | * | 5/1993 | Mercado et al. | 359/793 |
| 5,359,453 A | | 10/1994 | Ning | |
| 5,416,634 A | | 5/1995 | Ning | |
| 5,666,222 A | | 9/1997 | Ning | |
| 5,900,971 A | | 5/1999 | Ning | |
| 5,914,818 A | * | 6/1999 | Tejada et al. | 359/663 |
| 6,282,033 B1 | * | 8/2001 | Ning | 359/739 |
| 6,364,829 B1 | * | 4/2002 | Fulghum | 600/160 |
| 6,639,739 B1 | * | 10/2003 | Stone et al. | 359/793 |
| 2001/0056282 A1 | * | 12/2001 | Sonnenschein et al. | 606/139 |
| 2002/0071124 A1 | * | 6/2002 | Schwarz | 356/445 |
| 2003/0223632 A1 | * | 12/2003 | Freifeld | 382/152 |
| 2004/0090638 A1 | * | 5/2004 | Babayoff et al. | 356/609 |

FOREIGN PATENT DOCUMENTS

| | | |
|---|---|---|
| EP | 0587177 A1 | 3/1994 |
| WO | WO 93/00766 A1 | 1/1993 |
| WO | WO 93/17362 A1 | 9/1993 |

* cited by examiner

*Primary Examiner*—John P. Leubecker
(74) *Attorney, Agent, or Firm*—Michael C. Staggs; L. E. Carnahan; Alan H. Thompson

(57) ABSTRACT

An optic for the imaging optics on the distal end of a flexible fiberoptic endoscope or rigid borescope inspection tool. The image coverage is over a narrow (<20 degrees) field of view with very low optical distortion (<5% pin cushion or barrel distortion), compared to the typical <20% distortion. The optic will permit non-contact surface roughness measurements using optical techniques. This optic will permit simultaneous collection of selected image plane data, which data can then be subsequently optically processed. The image analysis will yield non-contact surface topology data for inspection where access to the surface does not permit a mechanical styles profilometer verification of surface topology. The optic allows a very broad spectral band or range of optical inspection. It is capable of spectroscopic imaging and fluorescence induced imaging when a scanning illumination source is used. The total viewing angle for this optic is 10 degrees for the full field of view of 10 degrees, compared to 40–70 degrees full angle field of view of the conventional gradient index or GRIN's lens systems.

9 Claims, 2 Drawing Sheets

OPTIC FOR INDUSTRIAL ENDOSCOPE/BORESCOPE WITH NARROW FIELD OF VIEW AND LOW DISTORTION

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to imaging optics, particularly to optics on the distal end of a flexible fiberoptic endoscope or rigid borescope inspection tool, and more particularly to an optic having a narrow (<20 degrees) field of view with very low optical distortion (<5% pin cushion or barrel distortion), while at the same time having a prescribed chromatic focal shift.

Current inspection methods depend upon either the visual judgement of a human operator and/or the costly and time consuming disassembly of complex or hazardous hardware. In industrial or laboratory settings, it can be either not cost effective or too hazardous to perform such work. In addition, the operators subjective visual judgement as to the condition of a component can depend upon factors such as lighting, visual fatigue or time available to make the determination. Also, the measurement of the surface roughness in the turbine blades of an electrical power generator, for example, can put a unit out of service for a significant time and reduce efficiency of the station and cause cost to increase to the end user as well.

For the inspection and measurement of surface roughness on the interior of mechanical constructions, it is not always possible to use optical interfero-metric or mechanical measurement techniques. Close, cramped spaces and the inability of disassembly forces this measurement to be made by other means. Typical surface metrology involves a stylus profilometer being drug across a surface for contact measurements. For non-contact measurements, white light phase shifting optical interfero-metric methods are used when the part can be transported to the interferometer. When such disassembly and transport are not possible or practical such as in-siter nuclear reactor fuel rod inspections, nuclear weapons pit inspections, medical settings, etc., other methods must be developed and employed.

The optics of this invention will allow data to be taken optically and post processed to gage material condition. The subsequent computer processing of this data can give a go/no go reading on surface topology and aid in the decision processes for further action. The optics of this invention is optimized for high spatial resolution, minimal nonlinear magnification distortion while at the same time having a prescribed chromatic focal shift. The image coverage is over a narrow (<20 degrees) field of view with very low optical distortion (<5% pin cushion or barrel distortion).

SUMMARY OF THE INVENTION

It is an object of the present invention to provide an imaging optic on the distal end of an inspection tool.

A further object of the invention is to enable inspection of the interior of a component.

A further object of the invention is to provide an optic designed to allow a very broad spectral band or range of optical inspection.

A further object of the invention is to provide an optic that is capable of spectroscopic imaging and fluorescence induced imaging when a scanning illumination source is used.

Another object of the invention is to provide an optic designed to allow conventional imaging with very low (<0.5%) optical distortion.

Another object of the invention is to provide an optic design to all non-contact surface roughness measurement.

Another object of the invention is to provide an optic designed to have a specific chromatic focal shift for focus, while maintaining the low distortion image.

Another object of the invention is to provide an optic having a narrow (<20 degrees) field of view.

Another object of the invention is to provide an optic having a total viewing angle of 10 degrees for the full field of view of 10 degrees.

Other objects and advantages of the present invention will become apparent from the following description and accompanying drawings. The invention involves an imaging optic for location on the distal end of an inspection tool, such as a flexible fiberoptic endoscope or rigid borescope. The image coverage of the optic is over a narrow (<20 degrees) field of view with very low (<5%) optical distortion, while at the same time having a prescribed chromatic focal shift. The chromatically shifted images are generated with a broad band visible spectrum illumination system. The images are collected by the optic and relayed either onto a coherent fiber optic image bundle of an endoscope or onto the image plane of the relay image sets of a rigid borescope. The image analysis will yield non-contact surface topology data for an inspection where access to the surface does not permit a mechanical stylus profilometer verification of surface topology. The optic may be made of fused silica to allow a very broad spectral band or range of optical inspection. This optic enables inspection of the interior of mechanical constructions, such as in-siter nuclear reactor fuel rod inspections, the interior of a nuclear weapons pit, jet engine turbine blades, the interior of industrial generator, and medical applications (in-siter/in-vivo inspections of cardiac or pulmonary scare tissue), as well as many other areas requiring non-contact inspection.

BRIEF DESCRIPTION OF THE DRAWINGS

The accompanying drawings which are incorporated into and form a part of the disclosure, illustrate embodiments of the invention and, together with the description, serve to explain the principles of the invention.

DETAILED DESCRIPTION OF THE INVENTION

The present invention is directed to an optic optimized for high spatial resolution, minimal nonlinear magnification distortion (pin cushion/barrel type optical distortion) while at the same time having a prescribed chromatic focal shift. It is this chromatic focal shift that is normally designed out of an optical system that is used to take the data required far non-contact surface roughness measurements. The chromatically shifted images are generated with a broad band visible spectrum illumination system. The images are collected by the optic and relayed either onto a coherent fiber optic image bundle of an endoscope, such as shown in FIG. 3, or onto the image plane of the relay image sets of a rigid borescope. The images are recorded onto the image plane of a color CCD camera, see FIG. 3. The composite video image is digitized and stored electronically with a frame grabber or other image recording device and then split into separate color image channels e.g., red 24, green 26, and blue 28 as shown in FIG. 3, to produce an image received from distinct image focal planes, see FIGS. 1 and 2. These images are a recording of the phase data produced from, for example, three focal planes, limited by the optical band pass of the color separation filters in the CCD camera image chip. Knowledge of the spectral centroid and FWHM of the data channel can aid in qualitative and quantitative description of the surface topology of the surface under investigation.

Figure 1:
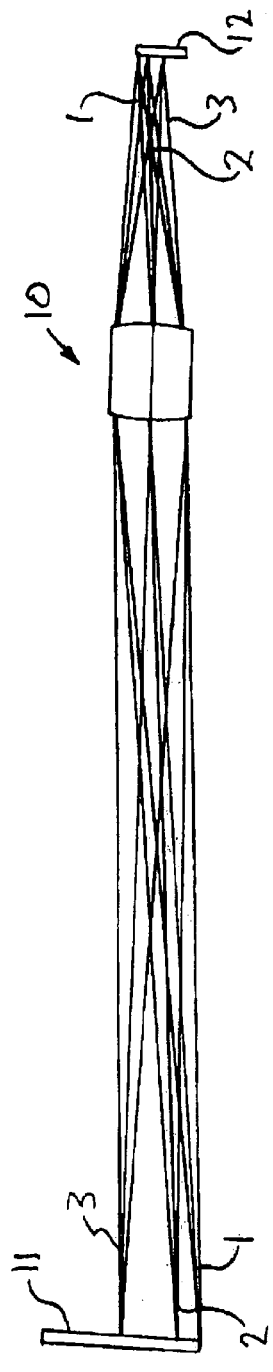
FIG. 1 is a cross-sectional side view of an embodiment of the optic of the invention mounted in an optic layout.

Referring now to the drawings, FIG. 1 is a cross-sectional view of an embodiment of the optic indication at 10. The optic 10, as shown in FIG. 1, is located intermediate an object or sample 11 and an image plate 12. Three(3) light segments 1, 2 and 3 are directed onto the object 11 and reflected back through the optic 10 and contact the image plate 12 in a 180° relation. The colors of the light segments 1–3, may be, for example, as seen on the object 11, red, green, and blue, with these colors being reversed or rotated 180° when seen on image plate 12 as light segments 1(red), 2(green) and 3(blue).

Figure 2:
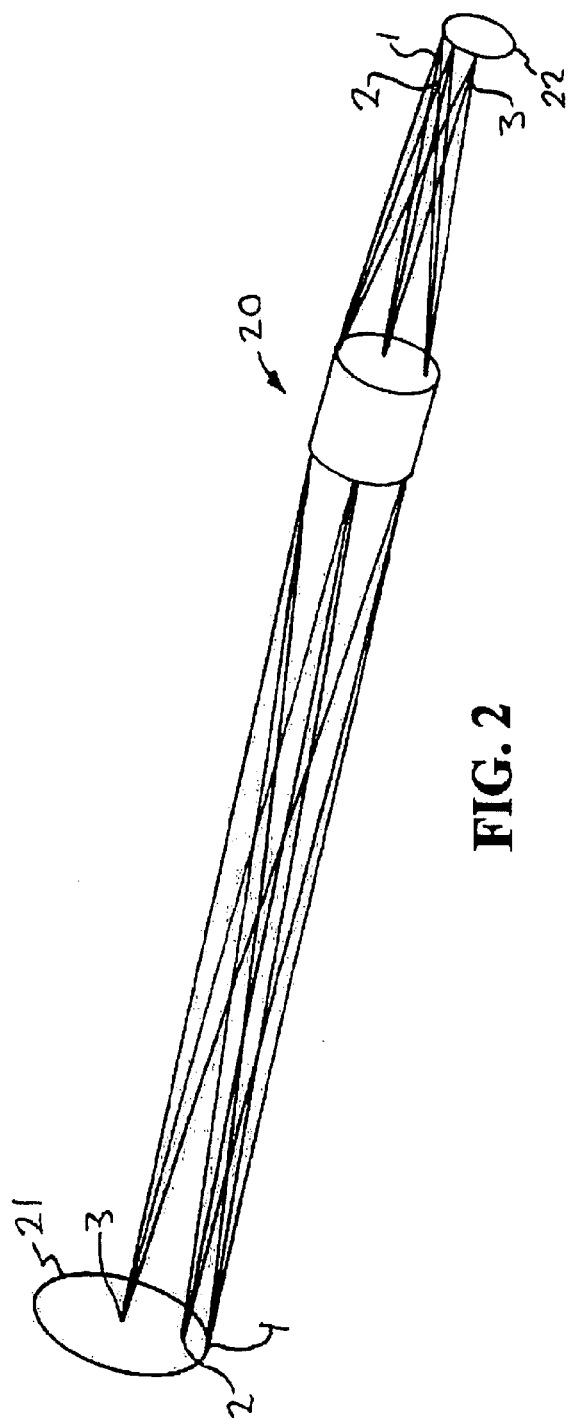
FIG. 2 is a 3D optical layout incorporating an optic made in accordance with the present invention.
Figure 3:
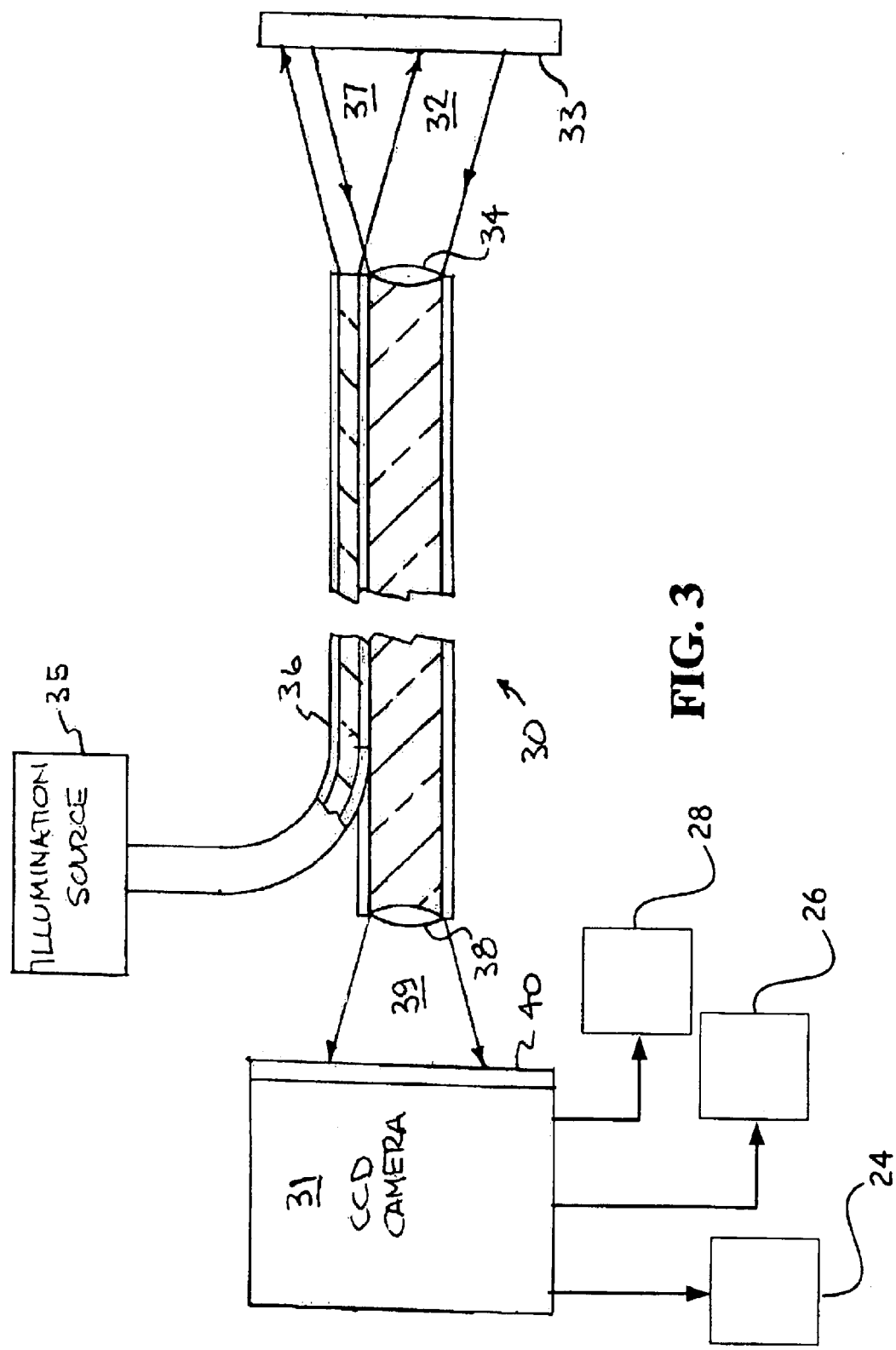
FIG. 3 illustrates, partially in cross-section, a fiberoptic endoscopic inspection tool with a camera as the viewing port detector, and which incorporates the optic of the present invention.

FIG. 2 illustrates a 3D embodiment of the optic of the invention generally indicated at 20 and mounted intermediate an object or sample 21 and an image plate 22, with the light segments 1–3 being illustrated as described above relative to FIG. 1.

As pointed out above, the optic of this invention was designed to allow conventional imaging with very low optical distortion (<0.5%) when compared to the majority of distal endoscope optics that are based on gradient index or GRIN's lens designs that have significant distortion (typically >20%). The low distortion was selected as a major requirement for the weapons inspection (interior of a nuclear weapons pit) as an undistorted image would allow the accurate mapping of features as the magnification would be nominally equal across the image field.

The design of the optic was chosen to allow non-contact surface roughness measurement based on an image system such as illustrated in FIG. 3, described hereinafter. The optic was designed to have a specific chromatic focal shift for focus, while maintaining the low distortion image. With the change in focus of an image, there is a change in the phase of the image at that image plane. By processing the images from a series of test coupons of varying roughness, covering a range above and below the expected test sample, a mathematical scalar can be derived that can select the range or bin that the roughness falls in between two of the test coupons. This technique was verified against roughness as measured by a mechanical stylus profilometer.

The field of view for this optic is narrow (<20 degrees) when compared to conventional distal imaging optics found on small endoscopes. The total viewing angle for this optic is 10 degrees for the full field of view (FOV) of 10 degrees. GRIN's lens system generally are from 40–70 degrees full angle FOV. The main use of this system is for specific metrology of surfaces rather than a survey tool as are nearly all small endoscopes.

FIG. 3 illustrates a commercial fiberoptic endoscope inspection tool generally indicated at 30 with a camera 31 as the viewing port detector. The endoscope tool 30 includes an image cone 32 positioned adjacent an object, surface, or sample 33, and includes an optic 34 at the distal end, which may be the optic of FIGS. 1 and 2. An illuminator 35 is connected via a single mode optical fiber 36 to a fiber illumination cone 37. An image lens 38 is mounted at the opposite end of endoscope tool 30 and the image 39 from the surface or object 33 is directed onto transited image planes 40 to the CCD camera 31.

As described above, FIG. 3 illustrates a commercial fiberoptic endoscopisc inspection tool with a camera as the viewing port detector. The camera image is relayed into a portable computer with a video frame capture capability. The portable computer has software to control the camera and perform the necessary documentation and image processing work to collect and determine the sample conditions (surface roughness and visual evidence of contamination). Computer software would determine the proper image planes based upon test sample coupons inspected and stored before the test began. An inspection procedure would begin by the operator inserting the endoscopic inspection instrument into the access prot of the device and locating the component parats to be viewed and measured. The computer would modulate the focal plane of the detector and collect images at predetermined places based upon the instrument optical calibration. The image plane modulation would be performed by real-time image processing to measure the change in processed signal of a line or series of lines across the sample. The change of focus of the image plane will be electric motor driven or pneumatically actuated with a feedback mechanism to trigger the TV camera frames at the precise positions. Lighting and lens parameters would be pre-determined on test samples imaged just prior to the test data collection. Amy changes in the optical instruments performance could be compensated in the field. The images of the in-focus and de-focused data would be stored on the computer for off-line processing. The operator would collect a series of images and the data processed by the computer giving a near real time determination of the quality or safety of a part in question. Removing the subjective determination by the human operator is one of the key aspects of this new inspection process.

Likewise, the inspection of stains or discoloration as a method to identify potential contaminants is also possible with this system. In this case, instead of focal position changes as the method to discriminate between good and bad surfaces, optical colorimetry will be used to measure defects. The imager used for this technique will be one that records a full color image of the sample. A lighting system capable of producing a spectral distribution matched to the detector CCD chip will be used. Software on the camera and in the portable computer will balance the response of the camera against the spectral output of the camera to produce a color balanced output image. The color separation filters in the imager head will be chosen to collect spectrally selective information about the surface in wavelength bands with minimal overlap. The photometric data produced by the inspection of test coupons just prior to the image collection of the data samples will be stored on the portable computer. The operator will collect test data and the computer will off-line process these images to determine those with suspected contamination.

It has thus been shown that the optic of this invention has an image coverage over a narrow (<20 degrees) field of view with very low optical distortion (<5% pin cushion or barrel distortion), while at the same time having a prescribed chromatic focal shift. The specific design of the optic will permit simultaneous collection of selected image plane data. This data will be then subsequently optically processed. The image analysis will yield non-contact surface topology data for an inspection where access to the surface does not permit a mechanical stylus profilometer verification of surface topology. The optic is particularly applicable for inspection of the interior of a nuclear weapon pit, in-siter nuclear reactor fuel rod inspections, insilu/invivo inspections of cardiac or pulmonary scare tissue, lead screw assemblies of jet engines, inspection of jet engine turbine blades, the interior of industrial generators, and inspection of improvised explosive devices for disarming purposes, as well as other inspections in close, cramped spaces.

While a particular embodiment of the invention, along with materials and parameters have been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. In an inspection tool utilizing an optic at a distal end, the improvement comprising:

said optic having a prescribed chromatic focal shift and an image coverage of <20 degrees field of view with an optical distortion of <5%, wherein said optical distortion comprises pin cushion or barrel distortion; and means for changing the focal plane of said optic to produce one or more images having phase and spectral information, wherein an image with surface topology and/or contamination characteristics can be constructed from the one or more images.

2. The improvement of claim 1, wherein said optic is constructed to image colors at a common optical plane with limited chromatic focal shift and limited lateral color shift.

3. The improvement of claim 1, wherein said optic has a total viewing angle of 10 degrees for a full field of view of 10 degrees.

4. The improvement of claim 1, wherein said optic has an optical distortion of <0.50%.

5. The improvement of claim 1, wherein said optic is mounted at a distal end of a fiberoptic endoscope inspection tool, and with a camera as a viewing port detector.

6. The inspection tool of claim 5, additionally including an endoscope image cone, wherein the optic additionally includes an endoscope image cone formed adjacent the optic.

7. The inspection tool of claim 5, additionally including an illuminator directing light via a single mode optical fiber to a fiber illumination cone located adjacent and at least partially overlapping an endoscope image cone.

8. The inspection tool of claim 7, wherein said single mode optical fiber extends along an external area of said endoscope inspection tool.

9. The inspection tool of claim 5, wherein said camera is a CCD camera.

* * * * *